United States Patent [19]

Hessel

[11] Patent Number: 5,263,935
[45] Date of Patent: Nov. 23, 1993

[54] PRESSURIZED FLUID DISPENSER

[75] Inventor: Stephen R. Hessel, Fountain Valley, Calif.

[73] Assignee: Baxter International Inc., Deerfield, Ill.

[21] Appl. No.: 689,986

[22] Filed: Apr. 23, 1991

Related U.S. Application Data

[60] Continuation-in-part of Ser. No. 935,021, Nov. 26, 1986, Pat. No. 4,769,008, which is a division of Ser. No. 561,242, Jul. 30, 1990, abandoned.

[51] Int. Cl.$^5$ .............................................. A61M 37/00
[52] U.S. Cl. ............................. 604/132; 128/DIG. 12; 604/131; 604/133
[58] Field of Search ............................ 604/131–133, 604/74–76, 246, 891.1, 141, 51; 128/DIG. 12; 222/211

[56] References Cited

U.S. PATENT DOCUMENTS

| | | | |
|---|---|---|---|
| 3,677,444 | 8/1972 | Merrill | 604/132 |
| 3,993,069 | 11/1976 | Buckles et al. | 604/132 |
| 4,201,207 | 6/1980 | Buckles et al. | 604/132 |
| 4,267,836 | 5/1981 | Whitney et al. | 604/246 |
| 4,386,929 | 6/1983 | Peery et al. | 604/132 |
| 4,419,096 | 12/1983 | Leeper et al. | 604/132 |
| 4,525,165 | 6/1985 | Fischell | 604/891.1 |
| 4,904,239 | 2/1990 | Winchell et al. | 604/132 |

Primary Examiner—Randall L. Green
Assistant Examiner—Rob Clarke
Attorney, Agent, or Firm—Paul E. Schaafsma; Amy L. H. Rockwell; Paul C. Flattery

[57] ABSTRACT

Disclosed is an elastomeric bladder infusion pump which may be used for delivering a pharmaceutically active material to a patient at a substantially constant flow rate. A unitary internal stress member or mandrel is disposed within the bladder, prestressing the bladder in both the axial and radial dimensions.

9 Claims, 3 Drawing Sheets

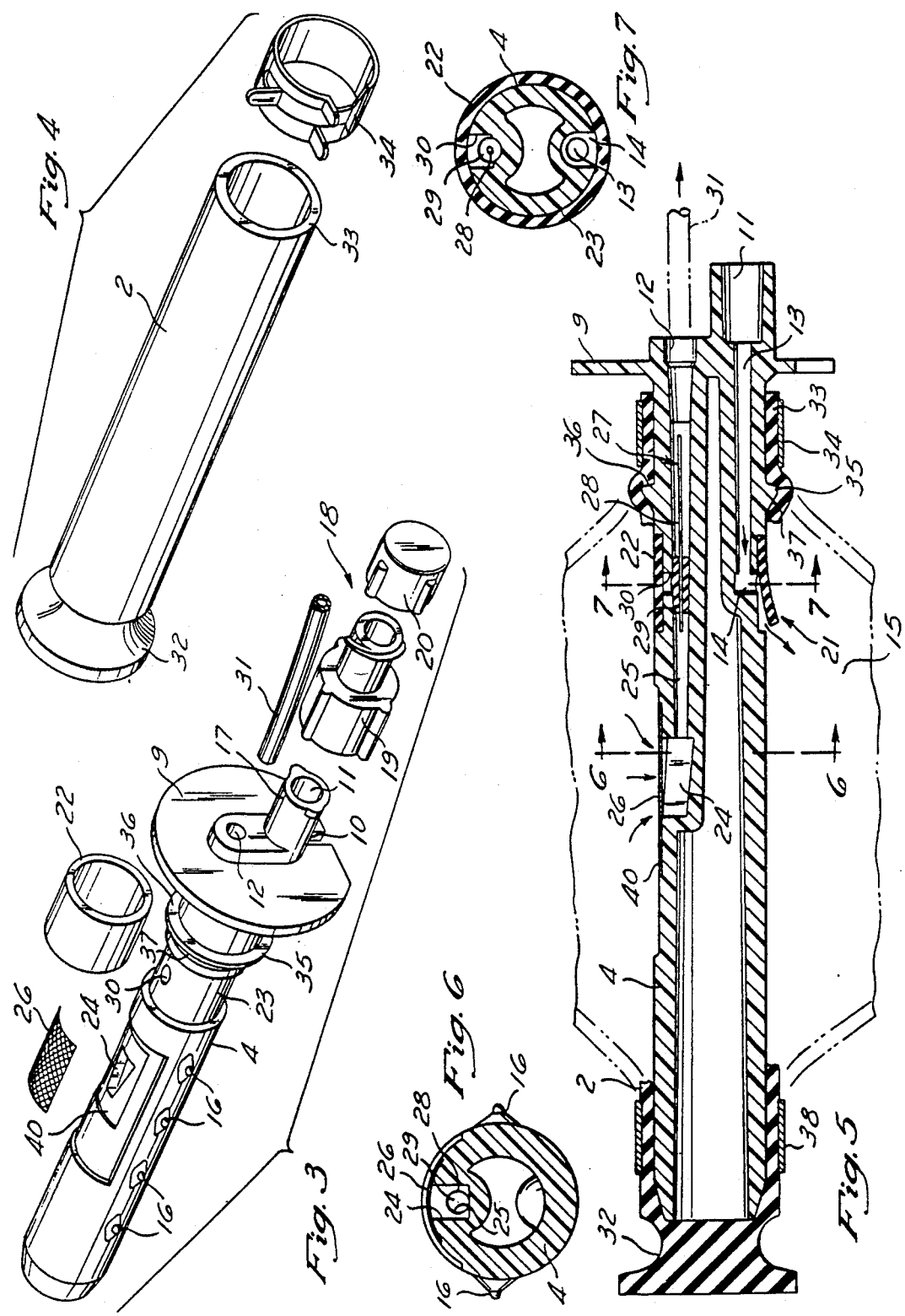

PRESSURIZED FLUID DISPENSER

BACKGROUND OF THE INVENTION

This application is a continuation in part of my prior copending application Ser. No. 935,021 filed Nov. 26, 1986, now U.S. Pat. No. 4,769,008, and a division of application Ser. No. 561,242, filed Jul. 30, 1990, now abandoned.

The present invention relates to a compact elastomeric bladder infusion pump for administering a pharmaceutically active material at a substantially constant flow rate over the service cycle of the pump. More particularly, the present invention relates to an improved infusion pump having an internal stress member disposed within the bladder, which prestresses the bladder in both the axial and radial directions, thereby enabling the bladder to exert a substantially constant pressure on the contents thereof throughout the service cycle. Although a variety of elastomeric bladder infusion pumps are known, there remains a need for an infusion pump which is simple and inexpensive from a manufacturing standpoint, yet is capable of delivering its contents at a substantially constant rate.

None of the prior art elastomeric bladder infusion pumps known to the inventor may be easily manufactured at a low per-unit cost, and yet exhibit a high degree of reliability in terms of storage life and the ability to deliver substantially all of the contents at a substantially constant flow rate.

SUMMARY OF THE INVENTION

The present invention provides an elastomeric bladder infusion pump. A significant feature of this invention is that the pump constructed in accordance with the invention delivers substantially all of the pharmaceutically active material contained therein at a substantially constant flow rate while being inexpensive, reliable and simple to manufacture.

In accordance with one aspect of the present invention, a portable infusion pump for delivering a quantity of pharmaceutically active material at a substantially constant flow rate has been provided. The infusion pump comprises an elastomeric bladder having at least one open end, and an elongate stress member extending concentrically within the entire length of the hollow portion of the bladder and having a fluid-tight seal therewith. Both a filling port and an exit port are provided on the stress member, each in fluid communication with the interior of the bladder by way of an influent and an effluent lumen, respectively. The stress member has a diameter that is greater than the relaxed internal diameter of the bladder, and has a length that exceeds the relaxed internal length of the hollow portion of the bladder, so that it prestresses the bladder in both the axial and radial directions when disposed therein, substantially filling the bladder in its unfilled state. Preferably, the axial stress imparted by the internal stress member is from about 35% to 60%, and the radial stress is preferably from about 15% to about 40%, measured as a percent increase in the specified dimension caused by the internal stress member, compared to that dimension on a completely relaxed bladder.

In accordance with a further aspect of the present invention, there has been provided an infusion pump having a single flow channel through at least a portion of the stress member and in fluid communication with the interior of the bladder through a first end thereof, and a closure member on a second end of the flow channel for preventing escape of the fluid contents under pressure in the bladder. The closure member preferably comprises a pierceable resealable septum. In a preferred embodiment, the infusion pump further comprises a support on the stress member for supporting the pierceable septum and for receiving a flow regulator thereon.

A removable flow regulator has been provided for controlling the rate of flow of a fluid medication stored under pressure in an elastomeric bladder infusion pump having a pierceable septum for retaining the fluid therein. The flow regulator comprises an elongate tubular body having a first and a second end and a flow path therebetween, and a first hollow needle secured to the first end of the tubular body and in fluid communication with the flow path. A flow restriction passageway is disposed within the flow channel for regulating the rate of flow therethrough, and the first hollow needle is provided with a pointed end for piercing the septum on the infusion pump thereby placing the flow restriction channel in fluid communication with the contents of the infusion pump.

An important feature of the infusion pump of the present invention is the provision of a one-way valve on the stress member which permits flow in the influent lumen only in the direction of the interior of the bladder. This one-way valve is a substantial advantage over the prior art in that it permits filling of the pump by any pressurized means having a luer connection thereon. Contrariwise, the prior art infusion pumps generally require piercing of a septum during the filling procedure.

In the preferred embodiment, a controlling means for regulating the effluent flow comprising a capillary tube of known internal diameter, is concentrically disposed within the effluent lumen through said internal stress member.

An additional feature of the invention is that the internal stress member is advantageously provided with a very simple, yet very effective, visual display when the bladder has been emptied a predetermined amount. As described hereinafter, a plurality of indicator bumps, spaced apart and extending in a radially outward direction, provide a visual indication that the bladder is nearing the end of its duty cycle.

In one embodiment of the present invention, a stainless steel filter is disposed upstream of the exit port, on the exterior of the internal stress member traversing the transverse effluent duct through which the interior of the bladder is in fluid communication with the effluent lumen.

Further objects, features and advantages of the present invention will become apparent from the detailed description of preferred embodiments which follows, when considered together with the attached figures.

BRIEF DESCRIPTION OF THE DRAWINGS

FIG. 3 is an exploded perspective view of the dual lumen internal stress member of the present invention.

FIG. 4 is a perspective view of one embodiment of the bladder of the present invention, in its uninflated state.

FIG. 5 is a partial, cross-sectional view of a preferred embodiment of the present invention. In this view, a portion of the bladder is shown in phantom.

FIG. 6 is a partially sectional view taken along the line 6—6 of FIG. 5, with some features omitted for clarity.

FIG. 7 is a partially sectional view taken along the line 7—7 of FIG. 5, with some features omitted for clarity.

DETAILED DESCRIPTION OF THE PREFERRED EMBODIMENTS

Figure 1:
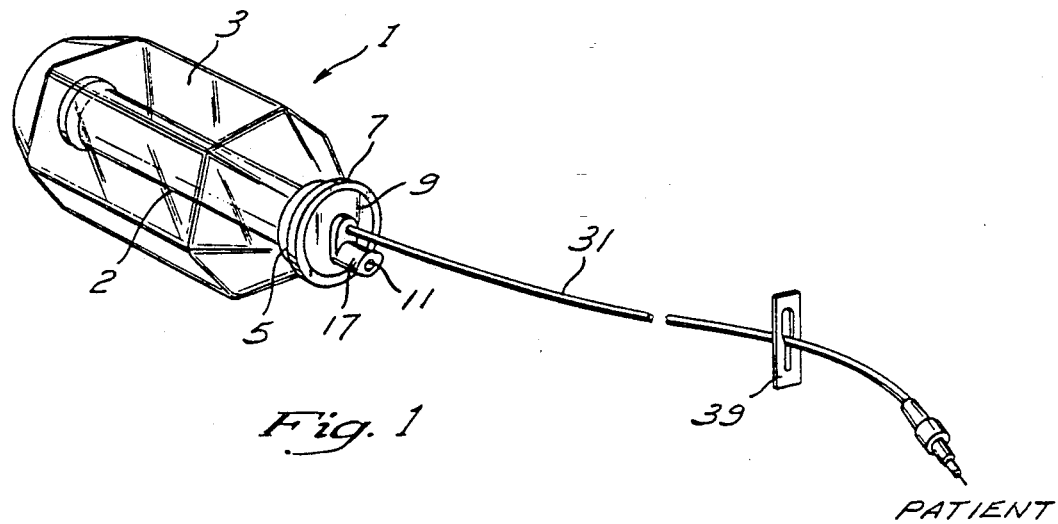
FIG. 1 is a perspective view of one embodiment of the infusion pump of the present invention.
Figure 2:
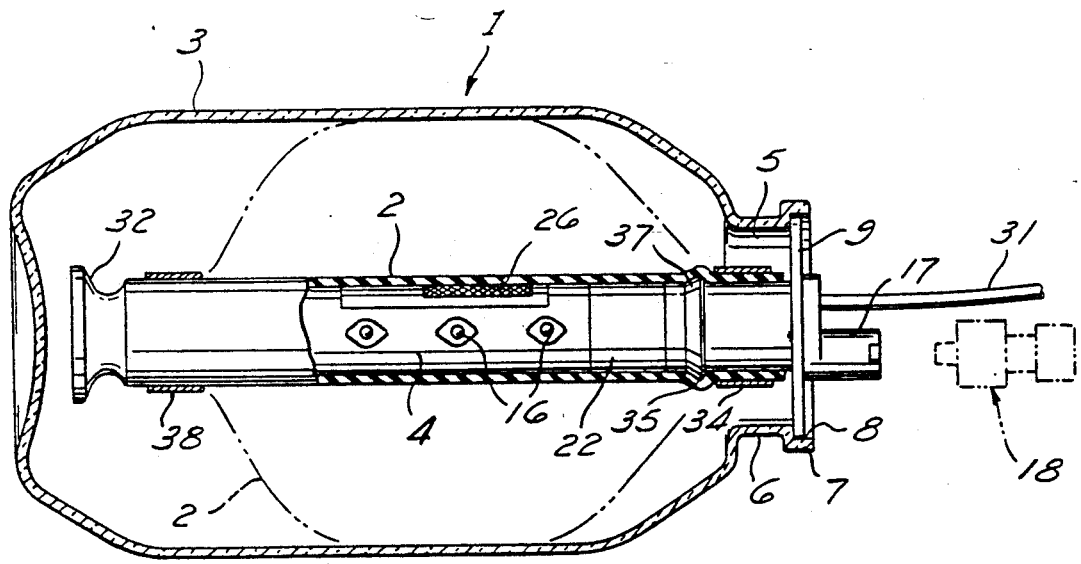
FIG. 2 is an elevational partial sectional view of the infusion pump of the present invention.

Referring to FIGS. 1 and 2, there is provided, in accordance with one aspect of the present invention, a constant pressure infusion pump 1 comprising an elastomeric collapsing bladder 2 disposed within a generally tubular outer casing 3 and concentrically about an internal stress member 4. The cross-sectional dimension of tubular casing 3 is selected so that it limits the radial outward expansion of bladder 2, thereby preventing rupture due to overstressing of the bladder by filling. The expanded state configuration of a preferred embodiment of the present invention is illustrated in phantora in FIG. 2. The bladder 2 may comprise any of a variety of elastomeric compositions well known in the art, which will be substantially inert in the presence of the pharmaceutically active material contained in the interior 8 thereof. By inert, it is meant that the material will not adversely react with or dissolve in the pharmaceutically active contents of the filled bladder, nor will it catalyze or initiate any deleterious reactions of that material.

For example, suitable vulcanized synthetic polyisoprenes are known in the prior art. Natural latex or silicone rubber having high resilience capabilities may also be used. Most preferably, the bladder comprises a blend of natural and synthetic rubbers having a high elasticity and low hysteresis. In any case, the bladder material is selected (1) to exert sufficient force on the fluid so as to expel substantially all of the contents of the bladder after having been filled and in storage, typically for some seven days or more, and (2) such that the infusion pump can be stored in the assembled (stressed) but not filled state for as much as a year or longer, without affecting the bladder's capability to expel its contents at a substantially constant rate.

The casing 3 is advantageously formed from any of a variety of known thermal distortion moldable polymeric materials, such as acrylic or styrene, which will protect the material of the bladder from ultraviolet light-initiated degradation, yet are substantially transparent to visible light, thereby permitting visual observation of the components of the infusion pump. Casing 3 is provided with an opening 5 at the proximal end thereof for receiving said internal stress member 4. Opening 5 has a neck 6 of lesser internal diameter than that of the axially directed annular flange 7, thereby forming an annular seating ring 8 for receiving a mounting disc 9 disposed near the proximate end of stress member 4. The disc 9 is provided with at least one perforation 10 therethrough, and may be mounted against the seating ring 8 using known clamps, adhesives or a friction snap fit.

A generally cylindrical internal stress member 4 comprises both a filling port 11 and an exit port 12 at the proximal end thereof, best illustrated in FIG. 5. Filling port 11, by way of lumen 13, and transverse influent duct 14, is in fluid communication with the interior 15 of the bladder 2. The stress member 4 may be produced in accordance with known thermoplastic forming techniques, and preferably comprises acrylic, styrene or any other rigid thermoplastic material that is substantially inert in the environment of the intended pharmaceutically active material. If it becomes desirable from a manufacturing standpoint, the stress member 4 may be formed from other materials and thereafter be provided with a continuous coating of an appropriate inert substance. Geometrically, the stress member 4 preferably has a substantially uniform circular cross section throughout that portion of its axial length disposed within the interior 15 of bladder 2, interrupted only by a plurality of indicator bumps 16, detailed infra.

Preferably, filling port 11 is provided with a male luer attachment 17 for connection to a filling apparatus. A double luer cap 18 is provided, which has a first female luer cap 19 for engagement with the male luer 17 on said filling port 11, and a second female luer cap 20 attached to said first luer cap 19. When luer cap 19 is removed for filling the bladder 2, the second luer cap 20 remains aseptic and may be detached from luer cap 19 for sealing filling port 11. Alternatively, luer 17 may be aseptically sealed with a sealing membrane instead of the double luer cap 18. The membrane may be removed at the time of filling, and, after filling, the filling port 11 may be sealed with a sterile standard size luer cap.

Backflow out of the transverse influent duct 14 of the material under pressure within the interior 15 of bladder 2 is prevented by one-way valve 21 comprising an elastic valve band 22 disposed coaxially about internal stress member 4 and in overlapping engagement with transverse influent duct 14. As illustrated in FIG. 3, the internal stress member 4 is provided with an annular recess 23 for receiving valve band 22 so that the outside diameter of valve band 22 is substantially the same as the diameter of the adjacent portions of the stress member 4. Thus, the generally cylindrical configuration of the stress member 4 with the valve band 22 in place is maintained, thereby permitting the deflated bladder 2 to snugly fit against stress member 4, minimizing spaces for trapped air in the infusion pump.

Pressure from an influent stream through transverse influent duct 14 will cause momentary displacement of elastic valve band 22, as illustrated in FIG. 5. As a result, the influent stream is permitted to pass into the interior 15 of bladder 2. Upon termination of the influent stream, valve band 22 will elastically return to sealingly obstruct duct 14, thereby preventing leakage of material from the interior 15 of bladder 2 back out through the transverse influent duct 14.

The interior 15 of bladder 2 is in fluid communication through transverse effluent duct 24 with effluent lumen 25 and exit port 12, disposed on the proximal end of stress member 4. In a preferred embodiment of the present invention, the lumen 25 extends in a distal direction through the stress member 4 at least far enough that effluent duct 24 is located near the center of the inflated bladder. Thus, in an embodiment wherein the inflated bladder 24 is approximately spherical, the effluent duct 24 is disposed approximately midway along stress member 4 between the proximal and distal points at which the axial is end regions of the bladder 2 are in sealing engagement with the stress member 4. Positioning effluent duct 24 away from the axial ends and near the midpoint of the interior space 15 of the bladder 2 reduces the likelihood that any air bubbles in bladder 2 will enter lumen 25 and be introduced into the patient.

Thus, the unitary stress member 4 has a first influent lumen 13 and a second effluent lumen 25 extending therethrough for introduction and removal, respectively, of material from the interior 15 of bladder 2. These lumen preferably are substantially parallel to each other, and each is provided with a port at the proximal end of the stress member 4.

Stress member 4 may further be provided with a screen or mesh 26 traversing effluent duct 24 and held in place by an adhesive, to preclude introduction into the patient of any pharmaceutical material that may have become crystallized during storage, or any other solid matter. Screen 26 may comprise stainless steel, platinum wire or other suitable metal, or any of a variety of polymers, such as polytetrafluoroethylene, having a porous or multifilament configuration capable of operating as a screen, and which will be substantially unreactive in the presence of the pharmaceutical material. The mesh size should be selected so that the sum of the flow paths through the mesh will permit sufficient flow that the mesh will not be a factor in the overall flow rate of the infusion pump. Placement of screen 26 may be anywhere near or downstream from duct 24, the illustrated preferred embodiment having been selected for ease of manufacture. The stress member 4 may be provided with a shallow depression 40 for receiving screen 26.

Effluent lumen 25 is further provided with a flow rate regulator 27, which may comprise capillary tube 28 having a lumen therethrough of known cross-section and length, disposed coaxially within effluent lumen 25. The regulator 27 regulates in a controlled manner the effluent stream against pressure developed from the bladder 2. Any of a variety of commercially available capillary tubes may be advantageously employed, such as glass capillary tubes or hypodermic needle stock. In order to accurately determine the flow rate of a given capillary tube, the precise internal radius of that tube is first determined. While the manufacturer's specifications are accurate enough for most capillary tube applications, small machining tolerances become important for the purpose of the present invention due to the known relationship that flow rate is proportional to the fourth power of the internal radius of a tube. The true radius of, for example, hypodermic needle stock having a specified I.D. of approximately 0.004 inch, is advantageously determined by first measuring the pressure drop through a tube of known length in dynes/cm². A gas maintained at a known pressure is directed through the capillary, and the pressure drop and flow rate empirically determined with the capillary discharging into normal atmospheric pressure. Having determined the flow rate and the pressure drop, as well as the length of the capillary tube, the internal radius of the capillary tube can be determined from Poiseuille's Law, as expressed in the equation:

$$Q=(Pr^4)/8Ln$$

where Q is the flow rate in cc/sec through the capillary tube, P is the pressure drop through the tube in dynes/cm², r is the internal radius of the tube in cm, L is the length of the tube in cm, and n is the viscosity in poise. Solving the equation provides the true internal radius of a given piece of capillary stock. Once the true internal radius is known, any desired flow rate can be inserted into the equation, from which the length of a piece of that capillary tube necessary to permit the desired f low rate is can be calculated. Thus, standard hypodermic needle stock can be appropriately cut to length to provide precise predetermined delivery rates such as anywhere from about 50 ml/hr or less to about 500 ml/hr or greater, including 100 ml/hr, 200 ml/hr, or any other desired rate.

The capillary tube 28 is advantageously secured within effluent lumen 25 by an adhesive material 29, as shown in FIG. 5, or a preformed member (not shown). Material 29 provides sealing engagement between the walls defining effluent lumen 25 and the regulator 27 to avoid any fluid communication around the outside of the capillary tube.

The stress member 4 is advantageously provided with a glue port 30 which allows exposure of a capillary tube 28 extending through effluent lumen 25 to the exterior for receiving a quantity of the adhesive 29, such as a urethane based, UV cured epoxy or other material that will be chemically inert in the presence of a pharmaceutically active material contained within the interior 15 of bladder 2 and will block any fluid communication through glue port 30.

Pharmaceutically active material contained within the interior 15 of bladder 2 is directed from regulating means 27 to the patient (not illustrated) by means of conventional I.V. tubing 31 sealingly attached to exit port 12.

Referring to FIG. 4, there is illustrated a preferred embodiment of the bladder 2 of the present invention, not intended as a scale representation, comprising an elastic, generally cylindrical member for defining a space which, in the unexpanded state, is of known interior cross-sectional and axial dimensions. The bladder 2 may be closed at the distal end 32 as shown. Alternatively, as described below, the bladder may be formed with an open distal end 32. The bladder 2 is open at the proximal or discharge end 33, the latter end being coaxially disposed about and in sealing engagement with internal stress member 4, as illustrated in FIG. 2. This seal is accomplished or enhanced by means of an annular clamp 34 extending therearound.

Distal to clamp 34 on internal stress member 4 is an annular flange or shoulder 35 which, in cooperation with clamp 34, prevent migration of the discharge end of bladder 2 in a distal direction due to elastic forces generated by the filled bladder, or by the axial prestressing of the empty bladder, which will be detailed infra. Annular flange 35 comprises a proximal surface 36 and a distal surface 37, which extend radially outwardly from said stress member 4 and converge to form a relatively sharp angle at the radially outward most portion of annular flange 35. As illustrated in FIG. 5, the distal surface 37 is inclined outwardly from the surface of stress member 4 at a more gradual angle than surface 36, thereby enhancing the securing function of annular flange 35. A similar result may be achieved without the use of annular flange 35, by providing stress member 4 with an annular depression (not illustrated) for receiving a clamp 34, an O-ring, or other conventional sealing means. The seal may alternatively be effected using any of a variety of known adhesives, such as an epoxy. In the embodiment illustrated in FIG. 5, the size of the annular flange 35 generally is minimized so that it is not a factor in the deflation characteristics of the bladder.

At the distal end of the bladder 2, there may be provided a second clamp 38, illustrated as an annular band, for clamping the distal end 32 of bladder 2 to the distal end of internal stress member 4 in sealing engagement. Use of this clamp will substantially eliminate any axial component of expansion of the bladder. Although the bladder 2 is illustrated in FIG. 4 as having been molded with a closed end at the distal end 32 thereof, use of clamp 38 also enables the use of bladders which have been extruded with an opening at each end and a central lumen extending therethrough.

The unexpanded length of bladder 2 is less than the axial length of that portion of stress member 4 disposed therein. Likewise, the unexpanded interior cross-sectional area of bladder 2 is less than the cross-sectional area of the portion of stress member 4 disposed therein. Thus, the bladder 2 is both axially and radially prestressed when concentrically disposed about stress member 4. It has been determined that prestress that is less than the prestress disclosed in the prior art optimizes the advantages of the present invention. Preferably, the axial prestress will be in the range of from about 35% or 38% to about 50%, meaning that the length of the portion of stress member 4 disposed within the mounted bladder is, for example, 48% longer than the relaxed length of the hollow portion of the bladder. More preferably, the axial prestress is from about 35% or 36% to about 44% or 45%, and most preferably it will be about 40%. Tests with axial stresses as high as 150% indicate that, although performance is acceptable, the unit is difficult to manufacture, and the elastic material of the bladder 2 does not favorably respond to storage at such a high stress. In addition, overstressed units tend to walk off of the stress member with time, and also, the adverse effects of degradation of the material of the bladder 2 are accentuated under a high axial or radial stress. Furthermore, too great an axial and/or radial stress has an adverse impact upon the filling capacity of the bladder 2. Axial prestressing of less than about 10-15% has been determined to be too low to produce the desired output flow rate when only small quantities of liquid remain in the bladder.

The radial prestress of the uninflated bladder is between about 10% and 100%, preferably is between about 15% and 40%, more preferably is between about 18% and 25%, and most preferably is about 20% or 22%. It has been determined that radial prestressing in excess of about 100% and less than about 5-10% present the same difficulties discussed in connection with over and under axial stressing.

Filling the system is advantageously accomplished by a syringe or other delivery apparatus, such as a variety of pumps commonly used by pharmacists, sealingly engaged in fluid communication with lumen 13, preferably by means of an appropriate luer for engaging a male luer 17 provided in filling port 11. For example, with a syringe containing the desired pharmaceutically active material in fluid communication with influent lumen 13, the syringe is compressed, generating a fluid pressure which pushes aside the valve band 22, thereby allowing fluid to enter the interior 15 of bladder 2 by way of transverse influent duct 14. The bladder 2 may be constructed to hold any desired amount of fluid. In one specific design of an infusion pump embodying the invention which has been constructed and successfully tested, the bladder was designed to hold a maximum volume of about 105 ml. Due to the prestressing of bladder 2, the system is capable of being charged with amounts less than the maximum capacity, and still delivering at the constant predetermined flow rate.

The bladder 2 and stress member 4 are preferably designed such that filling expands the bladder radially, but the axial length of the bladder 2 is essentially unchanged upon filling.

Upon release of pressure from the syringe, the resilient properties of the valve band 22 act in cooperation with fluid pressure generated by the stressed bladder, to close transverse influent duct 14, thereby preventing escape via lumen 13 of the pressurized pharmaceutically active material contained in the interior 15 of bladder 2. The fluid pressure within the fully extended bladder will likely be in the area of about 8-10 psi. Any air that may be trapped within effluent duct 24 or effluent lumen 25 may be expelled by way of tubing 31, and the effluent flow may then be stopped by means of a conventional tubing clamp 39 on tubing 31. The clamp 39 on effluent tubing 31 will normally be clamped before catheterization.

Upon release of a clamp on the tubing 31, the fluid pressure in the bladder will cause a known flow to occur through the capillary tube 28.

Due to the axial prestressing of bladder 2, a pressure profile generated by deflation of the bladder 2 will be substantially constant over the delivery volume. The radial prestress on the bladder 2 assures that the initial entry of the first 1-2 ml of fluid will immediately create maximum pressure to occur in the bladder 2, since essentially no fluid is necessary to bring the material of the bladder 2 to its elastic limit. An additional function of the prestressing of the bladder 2 is to ensure that the bladder is empty before it is filled with liquid, i.e., that no air will be disposed between the deflated bladder 2 and the adjacent exterior wall of internal stress member 4. The only air in the system will be that contained in the lumens 13, 25 and I.V. line 31, which can be expelled after filling the bladder and prior to catheterization. Thus, the likelihood of air being available for delivery to a patient is minimized, and only a minimal amount of the pharmaceutically active material will remain in the unit after infusion due to compression of the bladder 2 radially inwardly against stress member 4.

While the infusion pump of the present invention is in operation, the amount of pharmaceutically active material remaining in the bladder 2 at any time may, of course, be qualitatively evaluated by observing the size of the bladder 2 through the transparent material of outer casing 3. However, a more quantitative estimation of remaining service time is obtained by providing the internal stress member with a series of small indicator bumps 16 or raised areas along the surface thereof, which will only be visible when the bladder 2 shrinks back onto the stress member 4 in close conformity to the surface thereof. This plurality of raised indicator bumps 16 may be, for example, disposed in a colinear arrangement along the axial direction of the internal stress member 4, and spaced apart such that the sequential appearance of each bump during deflation of bladder 2 may be correlated with a particular volume of remaining pharmaceutical material in the bladder 2. Also, due to the predictability of the rate of discharge as a function of the diameter and length of capillary tube 28, it is possible to correlate the appearance of each of a series of raised indicators on the internal stress member with a particular time remaining between the time the indicator means becomes visible and the time that the pharmaceutical material has been completely expelled.

In accordance with a further embodiment of the present invention, there has been provided an infusion pump wherein influent lumen 13 and effluent lumen 25 of the above-described embodiment are combined into a single flow channel which is used for both loading and dispensing the fluid medication. The single lumen embodiments accrue all of the above-described advantages of both axial and radial prestressing of the elastomeric bladder, while at the same time permitting a somewhat simplified internal stress member. Construction materials and considerations being principally the same as described above, the following discussion will focus principally on the structural differences of the single lumen embodiments.

Figure 8:
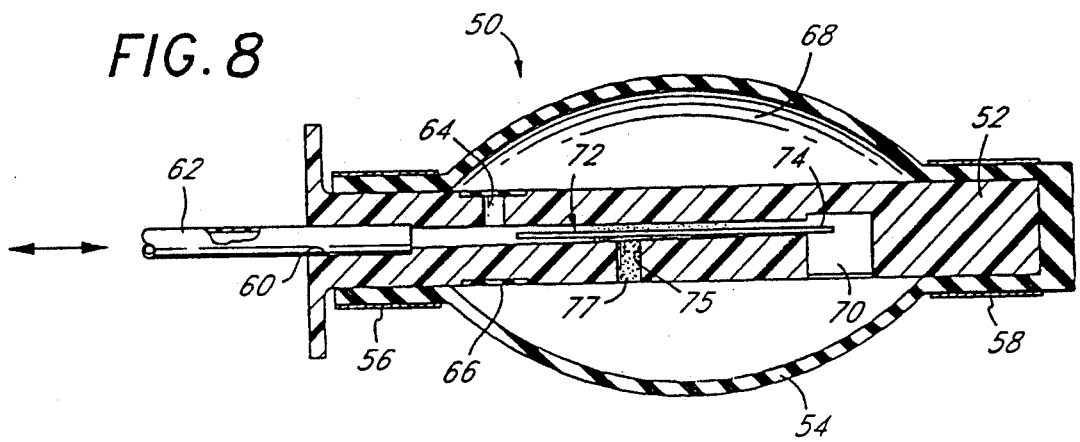
FIG. 8 is a simplified cross-sectional view of a first single lumen embodiment of the infusion pump of the present invention.

Referring to FIG. 8, there is disclosed an infusion pump 50 having an internal stress member 52 extending within and throughout the length of an elastomeric bladder 54. The relationships between the length and diameter of stress member 52 and the bladder 54 are the same as has been described in accordance with previous embodiments. Thus, for example, bladder 54 is secured at its proximal end by annular clamp 56 to provide a fluid-tight seal between the bladder 54 and the stress member 52. The clamp 56 may act in cooperation with an annular flange or shoulder 35 illustrated in FIG. 5, as will be appreciated by one of skill in the art, and other details illustrated in the prior embodiment may be incorporated into the single lumen design as well. For example, a distal annular clamp 58 may be provided to secure the distal end of the bladder 54 to the stress member 52.

In the single lumen embodiment illustrated in FIG. 8, the infusion pump 50 is loaded by connecting a source of pressurized fluid medication to the flow channel 60, preferably by way of tubing 62. Tubing 62 comprises any of a variety of known IV lines or other conduits for conveying a fluid medication. The proximal end of flow channel 60 may be appropriately dimensioned to receive tubing 62 therein, to be secured by a friction fit or by any of a variety of known adhesives which are suitable for contacting the medication conducted therethrough and will withstand sterilization conditions. Alternatively, any of a variety of interlocking structures may be provided for securing tubing 62 in fluid communication with flow channel 60.

Flow channel 60 is in fluid communication with the interior 68 of bladder 54 by way of both influent duct 64 and a flow controller 72. Influent duct 64 is in valved communication with the interior 68 of bladder 54 by way of a check valve 66, which in a preferred embodiment comprises an annular elastic check band as has been previously discussed. Other one way valves which can be envisioned by one of skill in the art may also be substituted therefor.

Thus, fluid entering flow channel 60 will pass through influent duct 64, past check valve 66 and into the interior 68 of bladder 54. Some fluid may additionally pass through flow controller 72 in a reverse direction, and into the bladder 54 by way of effluent duct 70. However, as the path of less resistance, fluid will favor influent duct 64 and may be loaded at a significantly greater rate therethrough than through the flow controller 72 alone.

Once the bladder 54 has received its intended volume of fluid, flow channel 60 is disengaged from the source of pressurized fluid medication, and check valve 66 prevents fluid from exiting bladder 54 by way of influent duct 64. Pressure generated from the contractile force exerted by bladder 54 causes fluid to traverse effluent duct 70, and back out of flow channel 60 by way of a flow controller 72. Flow controller 72 preferably comprises a flow restriction pathway of reduced cross-sectional dimension such as a hollow needle 74 as has previously been described; however, a "pin hole" or other orifice flow controller as may be envisioned by one of skill in the art, may be substituted therefor. In the preferred embodiment utilizing a flow control needle 74, the stress member 52 is provided with a glue port 75 for receiving a quantity of glue 77 to secure flow control needle 74 in the flow channel 60 and prevent fluid from bypassing needle 74. Although provision of a glue port 75 is convenient from a manufacturing standpoint, other means for securing the flow controller 72 may be envisioned, such as thermal deformation of stress member 52. Tubing 62 may be further provided with a standard pinch valve or other clamp (illustrated in FIG. 1) to stop the flow of medication.

Figure 9:
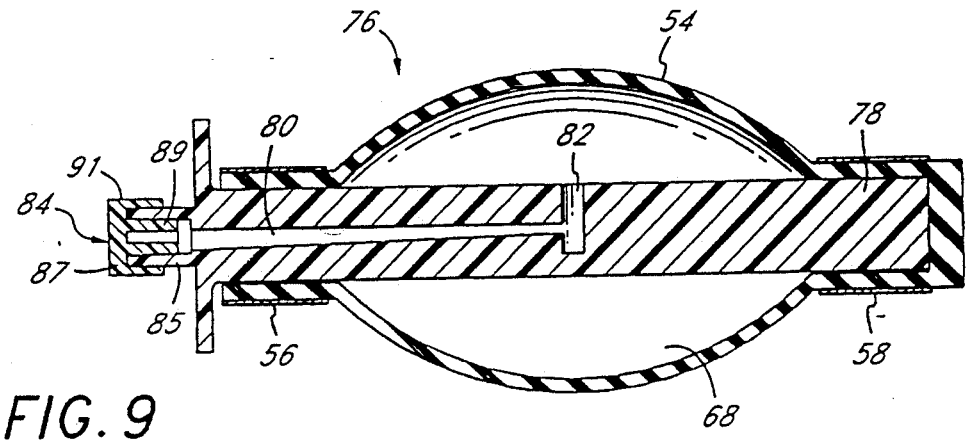
FIG. 9 is a simplified cross-sectional view of a second single lumen embodiment of the infusion pump of the present invention.

Referring to FIG. 9, there is provided still a further embodiment of the present invention, adapted for use with a removable flow regulator unit. In this embodiment, the infusion pump 76 is provided with stress member 78 disposed within bladder 54 and secured thereto by clamp 56 and clamp 58, as has been previously discussed. The stress member 78 is provided with a single flow channel 80 therethrough for both loading and dispensing medication, communicating with the interior 68 of bladder 54 by way of a duct 82. Duct 82 in FIG. 9, and effluent duct 70 in FIG. 8 are preferably each provided with a filter as has been described in accordance with previous embodiments.

Flow channel 80 is also provided with a closure member 84, which preferably comprises a pierceable, resealable septum as is well known in the art. For this purpose, and to provide a coupling for the removable flow regulator unit, which will be discussed, stress member 78 is provided at its proximal end with an axially extending annular flange which forms a generally cylindrical support 85. This configuration enables the use of a molded septum cap 87 as the closure member 84, as is illustrated in cross section in FIG. 9. The septum cap may be securely adhered, such as by the use of adhesives, to the support 85 to create a fluid impermeable barrier on the end of flow channel 80.

The septum cap 87 is preferably formed having a first cylindrical portion 89 extending therefrom for engaging the interior surface of cylindrical support 85 on stress member 78. Septum cap 87 is additionally preferably formed having a second cylindrical portion 91 spaced radially apart from and substantially concentrically about first cylindrical portion 89, for extending along the exterior surface of support 85. This structure enables a fluid-tight seal between the septum cap and flow channel 80 as well as providing a support for the flow regulator 86 illustrated in FIG. 10. Of course, numerous additional structures can be designed for both the support 85 and the flow regulator 86 for securing the support 85 and the flow regulator 86 in fluid communication with each other.

Figure 10:
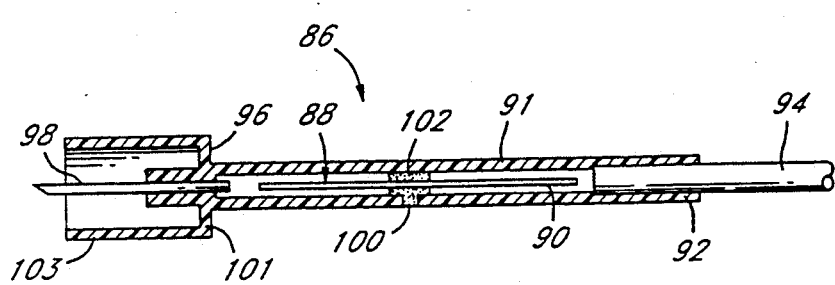
FIG. 10 is a cross-sectional view of a detachable flow regulator adapted for use with the infusion pump illustrated in FIG. 9.

Referring to FIG. 10, there is disclosed a removable flow regulator 86 for use in combination with the infusion pump 76 illustrated in FIG. 9. The flow regulator 86 comprises an elongate tubular body 91 having an opening at each of proximal end 96 and distal end 92, and a flow channel extending therebetween. The tubular body 91 may be produced in accordance with known thermoplastic forming techniques, and preferably comprises acrylic, styrene or any other rigid thermoplastic material that is substantially inert in the environment of the intended pharmaceutically active material. Suitable materials and manufacturing details will be apparent to those of skill in the art.

A flow controller 88 is disposed in the flow channel of tubular body 91, for precisely regulating the flow of fluid therethrough. Flow controller 88 is preferably a capillary tube or needle 90, as has previously been described. In that event, tubular body 91 is provided with a glue port 100 for receiving a quantity of glue 102 to secure the needle 90 as has been described.

In the embodiment of the flow regulator 86 illustrated in FIG. 10, the flow channel in the area of distal end 92 is dimensioned to receive tubing 94 for conducting medication to the patient. Tubing 94 may be friction fit or secured by a positive interlocking structure such a luer lock. Preferably, however, tubing 94 is inserted concentrically within an expanded region of the flow channel at the distal end 92 of body 91 and secured thereto by the use of a suitable adhesive.

Proximal end 96 of the tubular body 91 is provided with a structure adapted to cooperate with the support 85 of infusion pump 76. In particular, the flow regulator 86 is provided with an annular shoulder 101 extending radially outward therefrom and terminating at a tubular coupling 103 adapted for receiving the closure member 84 on infusion pump 76. Disposed within coupling 103 is hollow needle 98 which is in fluid communication with tubing 94 by way of the flow channel through flow regulator 86. Hollow needle 98 is preferably distinct from flow control needle 90, and needle 98 typically has a larger internal cross-sectional area so that needle 90 will be the principal flow regulating structure. Needle 9P can be molded directly to the tubular body 91, as illustrated, or affixed by an adhesive or other means. The gauge of needle 98 will typically be larger than needle 90 for the additional reason that it must exhibit sufficient strength to easily pierce closure member 84.

Coupling 103 and needle 98 are situated such that axial movement of the proximal end 96 of flow regulator 86 towards the septum cap 87 on infusion pump 76 enables hollow needle 98 to pierce the resealable septum cap 87, thereby placing tubing 94 in fluid communication with the interior 68 of bladder 54. Coupling 103 acts as a guide for needle 98, as well as to permit f low regulator 86 to snugly interf it with the support 85 of infusion pump 76. Flow regulator 86 and infusion pump 76 may further be provided with mechanical interlocking structures (not illustrated) such as a bayonet mount or luer connection, to further reduce the likelihood of accidental disengagement of the flow regulator 86 from infusion pump 76.

In this embodiment, the infusion pump 76 may conveniently be stored in the filled state, with the fluid being retained by closure member 84. The infusion pump 76 may be filled either by piercing the closure member 84 with a loading needle or cannulae, or by loading the bladder 54 prior to attachment of the closure member 84. The tubing 94 may be closed by way of a standard IV line clamp, and then flow regulator 86 inserted on to the end of infusion pump 76 thereby piercing septum cap 87 by hollow needle 98. Opening of the pinch valve on tubing 94 will commence the flow of medication.

Although this invention has been described in terms of certain preferred embodiments, other embodiments that are apparent to those of ordinary skill in the art are also within the scope of this invention. Accordingly, the scope of the invention is intended to be defined only by reference to the appended claims.

What is claimed is:

1. An infusion pump for delivering a quantity of fluid material at a substantially constant flow rate, comprising:
    an elongate elastomeric bladder having a central lumen and at least one open end, said central lumen having an internal length dimension and an internal diameter dimension in its relaxed state;
    an elongate stress member, said stress member extending throughout the length of and within the central lumen of the bladder;
    said stress member having a length dimension which is greater than the relaxed internal length of the central lumen on the elastomeric bladder, and said stress member having a diameter which is greater than the relaxed internal diameter of the central lumen on the elastomeric bladder;
    a flow channel in fluid communication with the interior of said bladder; and
    a flow regulator removably positioned in fluid communication with the flow channel,
    wherein the assembly of the elastomeric bladder onto the stress member prestresses the bladder in both the axial and radial directions prior to introduction of any of the fluid material into the bladder, and the axial length of the bladder is substantially unchanged upon filling with said fluid material.

2. An infusion pump for delivering a quantity of fluid material at a substantially constant flow rate, comprising:
    an elongate elastomeric bladder having a central lumen and at least one open end;
    an elongate, unitary stress member extending throughout the length of and within the lumen of the bladder, the stress member prestressing the bladder in both the axial and radial directions and having a substantially uniform maximum cross-sectional dimension throughout;
    a flow channel through at least a portion of the stress member and in fluid communication with the interior of the bladder through a first end thereof; and
    a closure member on a second end of the flow channel for preventing escape of fluid contents under pressure in the bladder.

3. An infusion pump as in claim 2, wherein the closure member comprises a pierceable, resealable septum.

4. An infusion pump as in claim 3, further comprising a support on the stress member for receiving a flow regulator thereon.

5. An infusion pump as in claim 4, further comprising a flow regulator mounted on the support and in fluid communication with the flow channel by way of a hollow needle extending through the pierceable septum.

6. An infusion pump as in claim 5 wherein the flow regulator is removably mounted on the support.

7. An infusion pump as in claim 5, wherein the flow regulator comprises an elongate tubular body having a flow channel therethrough; a hollow needle in communication with the flow channel, adapted for piercing the septum; and a flow restriction passageway in the flow channel for controlling the rate of flow therethrough.

8. A flow regulator for controlling the rate of flow of a fluid medication stored under pressure in an elastomeric bladder infusion pump having a pierceable septum for retaining the fluid therein, comprising:
- an elongated, tubular body having first and second ends and a flow path therebetween;
- a first hollow needle secured to the first end of the tubular body and in fluid communication with the flow path;
- a flow restriction passageway in the flow channel for regulating the rate of flow therethrough;
- wherein the first hollow needle is provided with a pointed end for piercing the septum on the infusion pump thereby placing the flow restriction passageway in fluid communication with the contents of the infusion pump, the tubular body further comprises a glue port extending therethrough, and the flow restriction passageway is a passageway through a second hollow needle secured within the flow path through the tubular body by a quantity of glue received through the glue port.

9. An infusion pump for delivering a quantity of fluid material at a substantially constant flow rate, comprising:
- an elongate elastomeric bladder having a central lumen and at least one open end, said central lumen having an internal length dimension and an internal diameter dimension in its relaxed state;
- an elongate stress member, said bladder, said stress member extending throughout the length of and within the central lumen of the bladder;
- said stress member having a length dimension which is greater than the relaxed internal length of the central lumen on the elastomeric bladder, and said stress member having a diameter which is greater than the relaxed internal diameter of the central lumen on the elastomeric bladder;
- a flow channel in fluid communication with the interior of said bladder; and
- a flow regulator in fluid communication with the flow channel, said flow regulator comprising an orifice having a predetermined cross-sectional dimension,
- wherein the assembly of the elastomeric bladder onto the stress member prestresses the bladder in both the axial and radial directions prior to introduction of any of the fluid material into the bladder, and the axial length of the bladder is substantially unchanged upon filling with said fluid material.

* * * * *